(12) United States Patent
List et al.

(10) Patent No.: US 8,114,028 B2
(45) Date of Patent: Feb. 14, 2012

(54) ANALYSIS SYSTEM FOR DETERMINING AN ANALYTE IN A BODY FLUID AND DISPOSABLE INTEGRATED SAMPLE ACQUISITION AND ANALYSIS ELEMENT

(75) Inventors: Hans List, Hesseneck-Kailbach (DE); Volker Zimmer, Morbach (DE); Michael Keil, Ludwigshafen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 397 days.

(21) Appl. No.: 12/548,479

(22) Filed: Aug. 27, 2009

(65) Prior Publication Data
US 2010/0036282 A1 Feb. 11, 2010

Related U.S. Application Data

(63) Continuation of application No. PCT/EP2008/001726, filed on Mar. 5, 2008.

(51) Int. Cl.
*A61B 5/00* (2006.01)
(52) U.S. Cl. .................................... 600/583
(58) Field of Classification Search .................. 600/573, 600/583
See application file for complete search history.

(56) References Cited

U.S. PATENT DOCUMENTS

| | | | |
|---|---|---|---|
| 5,660,791 A | 8/1997 | Brenneman et al. |
| 6,159,747 A | 12/2000 | Harttig et al. |
| 6,534,017 B1 | 3/2003 | Bottwein et al. |
| 6,827,899 B2 | 12/2004 | Maisey et al. |
| 2003/0050627 A1 | 3/2003 | Taylor et al. |
| 2003/0212345 A1 | 11/2003 | McAllister et al. |
| 2005/0036909 A1 | 2/2005 | Erickson et al. |
| 2005/0277850 A1 | 12/2005 | Mace et al. |
| 2010/0056893 A1 | 3/2010 | List |

FOREIGN PATENT DOCUMENTS

| | | |
|---|---|---|
| EP | 0863401 A1 | 9/1998 |
| EP | 0974061 A1 | 1/2000 |
| EP | 1285629 A1 | 2/2003 |

(Continued)

*Primary Examiner* — Jeffrey G Hoekstra
(74) *Attorney, Agent, or Firm* — Kristina E. Swanson; Roche Diagnostics Operations, Inc.

(57) ABSTRACT

An analyte determination analysis system with a disposable integrated sample acquisition and analysis element is disclosed. A piercing element has a tip for generating a bodily puncture wound and a test strip having a body fluid sample receiving zone to perform an analysis on a body fluid sample. A reusable analysis instrument comprises a coupling unit that couples the integrated sample acquisition and analysis element to a drive that drives a piercing element in a piercing movement comprising two phases: a propulsion phase wherein the piercing element moves on a puncture path in a puncture direction and a retraction phase wherein the piercing element moves opposite to the puncture direction after reaching a reversal point. A measuring and analysis unit measures a variable characteristic for the determination of the analyte and determines a desired analysis result on the basis of the measurement. The sample receiving zone of the test strip forms a sample contact. The piercing element, located parallel to the test strip, moves on a movement path relative to the test strip a puncture path. The piercing element, located adjacent to the sample contact, has a capillary channel with a sample inlet for body fluid entry after the piercing and a sample outlet for body fluid exit. The piercing element movement has a sample transfer position wherein the sample outlet is adjacent to the sample receiving zone such that the body fluid may be transferred from the capillary channel through the sample outlet to the sample receiving zone.

17 Claims, 8 Drawing Sheets

FOREIGN PATENT DOCUMENTS

| | | |
|---|---|---|
| EP | 1358844 A1 | 11/2003 |
| EP | 1276412 B1 | 12/2005 |
| EP | 1402812 B1 | 3/2006 |
| EP | 1360935 B1 | 12/2006 |
| EP | 1374770 B1 | 11/2007 |
| WO | 2005/112742 A2 | 12/2005 |
| WO | 2006/027101 A1 | 3/2006 |
| WO | 2006/092281 A2 | 9/2006 |
| WO | 2007/025713 A1 | 3/2007 |

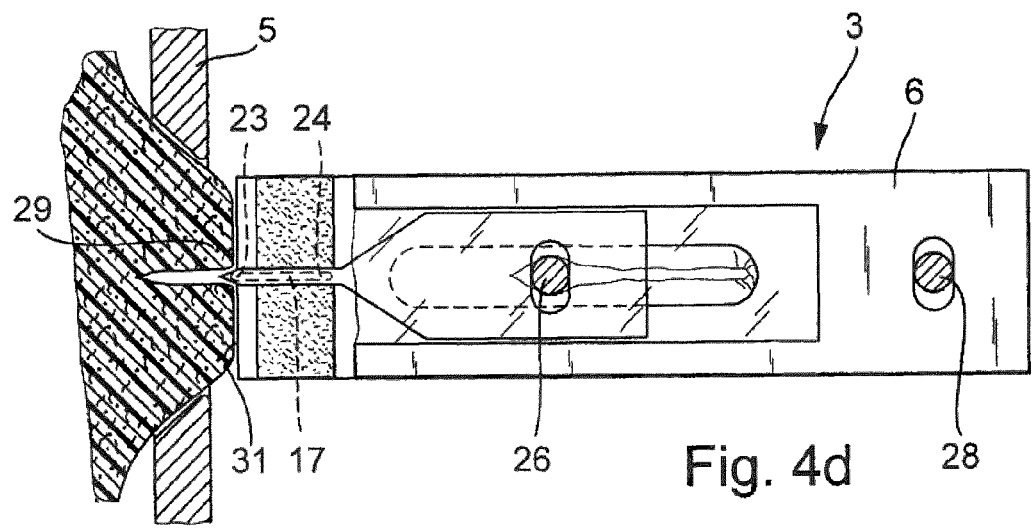
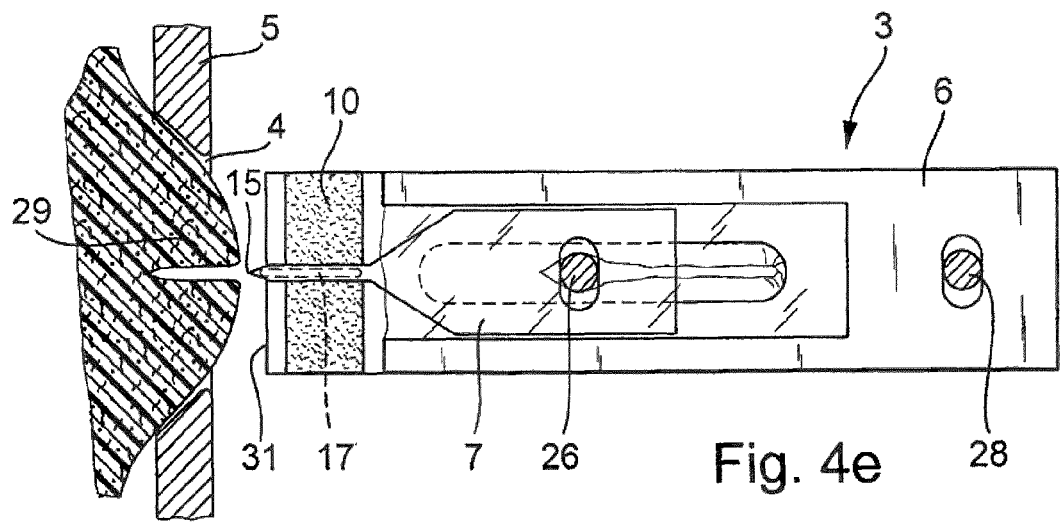
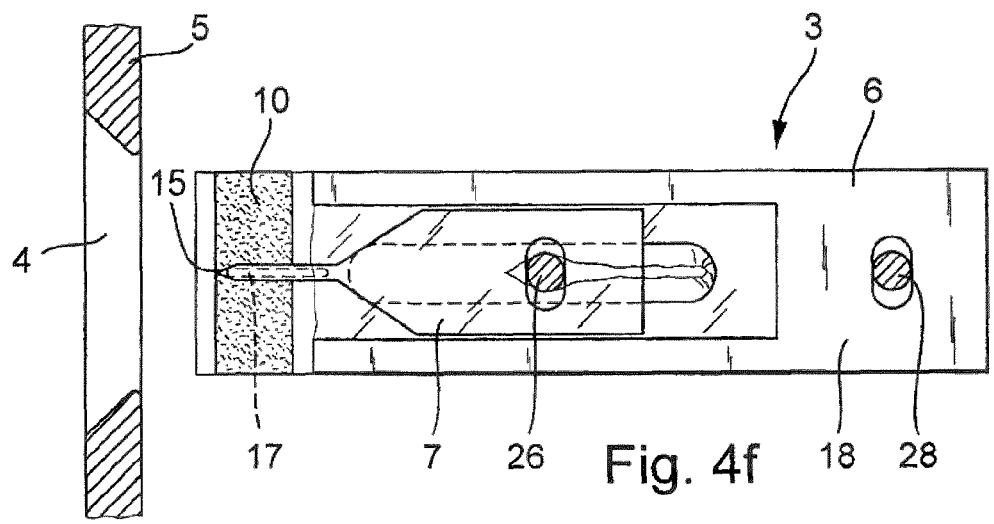

ANALYSIS SYSTEM FOR DETERMINING AN ANALYTE IN A BODY FLUID AND DISPOSABLE INTEGRATED SAMPLE ACQUISITION AND ANALYSIS ELEMENT

CROSS-REFERENCE TO RELATED APPLICATIONS

This application is a continuation of International Application No. PCT/EP08/001,726, filed Mar. 5, 2008, which claims priority to EP 07 005 222.0, filed Mar. 14, 2007.

BACKGROUND

The present disclosure relates to an analysis system for determining an analyte in a body fluid having a disposable integrated sample acquisition and analysis element and having a reusable analysis instrument.

For diagnostic purposes, small quantities of body fluids, such as blood, are taken from a body part. For this purpose, piercing devices having lancets are typically used, such devices generate a wound in the body part, for example, in the finger or in the ear lobe. The piercing systems are implemented in such a manner that they may also be used by laymen.

However, when determining an analyte in the body fluid, a procedure in multiple steps is required. Firstly, a wound must be generated in the body part using a piercing system, which comprises a piercing device and a lancet. A body fluid, such as, for example, blood, then exits from the wound. In a further step, the fluid must be received by a test element and supplied to an analysis system, which determines the desired analyte in the body fluid.

This procedure is complex, in particular for diabetics, who must determine the glucose content in the blood multiple times a day. Therefore, in addition to pain-free piercing as much as possible, increased operating comfort is also required.

In order to come one step closer to the desired operating comfort, integrated analysis systems have been proposed in the prior art, which also comprise an analysis unit in addition to a piercing device. An analysis system is known from WO 2006/027101 A1, in which, after the generation of the wound in the body part, the piercing device is moved away from an opening of the analysis system and an analysis unit is moved to the opening of the system in a second step, so that blood exiting from the wound can be received by the analysis unit.

In order to improve the handling ability and the comfort of the analysis systems, analysis systems have been developed which propose test elements and/or test sensors having an integrated lancet.

For example, an analysis system having a test sensor with an integrated lancet, in which an analyte in a body fluid is determined by an electrochemical measurement is known from WO2006/092281. The disposable test sensor comprises a test strip, on whose top side a capillary channel is provided, which is used to transfer the received body fluid to test electrodes, which are also located on the top side of the test strip, in order to determine an analyte in the body fluid. A lancet is located on the bottom side of the test strip, which is movably mounted relative to the test strip. The lancet is enclosed by a sterile envelope, from which it exits before piercing into the body part.

For the sample acquisition, the test sensor is guided into the vicinity of the opening of the analysis system. The lancet is then moved forward in the puncture direction until it exits from the opening of the receptacle system and generates a wound in a body part which is pressed against the opening. After the puncture, the lancet is retracted again until it is positioned in its sterile protective envelope again. The blood exiting from the puncture wound and/or the exiting body fluid is suctioned in by the capillary channel on the top side of the test strip and finally reaches the electrodes, so that an analyte in the body fluid may be determined electrochemically.

A system of this type has the disadvantage that two separate handling steps are necessary in order to, on the one hand, ensure the puncture in the skin and, on the other hand, ensure the transfer of a sufficiently large blood sample onto the test element.

This may be performed manually, after execution of the puncture, the analysis system being removed from the body part and the body part subsequently being "milked" in order to promote the escape of blood from the wound. As soon as a sufficiently large quantity of blood has exited from the wound, the analysis system is guided back to the wound manually in order to suction the sample into the capillary channel. This requires cumbersome handling by the patient and is difficult in particular for older people, who are frequently affected by diabetes. Alternatively to the manual procedure and the operation comprising multiple steps, the "milking" may be mechanized by the analysis system itself. For this purpose, systems having a so-called finger cone have been proposed. After the piercing procedure, the expression of a liquid sample is caused by pressure on the cone. For this purpose, the manual handling is thus replaced by a corresponding instrument function, which requires significant design effort and makes the instruments more costly, however.

As a third, rather theoretical possibility, which is also opposed by the demand for piercing with as little pain as possible, the lancet may be pierced so deeply into the body part that a sufficiently large blood droplet exits without additional measures such as manual or mechanical milking. The pain connected with the deep piercing is so great, however, that a system of this type is unsuitable for practice.

Therefore, there is a need for an analysis system which is distinguishable from the prior art by a high comfort for the user, in particular in that he only has to hold the analysis system on the body part once in order to determine the desired analyte. In addition, the analysis system will be easy to operate and will be based on a simple and cost-effective design.

SUMMARY

The present disclosure relates to an analysis system for determining an analyte in a body fluid having a disposable integrated sample acquisition and analysis element, which is also referred to as a "disposable or disposable item", and having a reusable analysis instrument. The disposable sample acquisition and analysis element can comprise a piercing element having a tip for generating a puncture wound in a body part and a flat test strip having a sample receiving zone for receiving a body fluid sample exiting from the puncture wound for analysis. The reusable analysis instrument can comprise a coupling unit for coupling a sample acquisition and analysis element (i.e., the disposable") to a drive, by which a puncture movement of the piercing element of the disposable is driven. The piercing movement can comprise a propulsion phase in which the piercing element can be moved on a puncture path in the puncture direction and a retraction phase in which the piercing element can be moved opposite to the puncture direction after reaching the reversal point of the puncture movement. The analysis instrument can also comprise a measuring and analysis unit for measuring a measurement variable which can be characteristic for the determination of the analyte and for determining a desired analysis results based on the measurement. The sample receiving zone of the test strip can be located on one of its flat sides, which forms a sample contact side. The piercing element can be located parallel to the test strip and can be movable relative to the test strip on a movement path during at least a part of the puncture movement.

Reference is made hereafter to blood as an example of a body fluid, without restriction of the generality. Of course, it can also be possible using the system according to the disclosure to determine analytes in other body fluids.

The sample receiving zone of the test strip of the disposable (i.e., throwaway) can be located on one of the flat sides of the test strip. This flat side can form a sample contact side. The piercing element can be located parallel to the test strip and can be movable on a movement path relative to the test strip during at least a part of the puncture movement. The piercing element can be located close to the sample contact side of the test strip of the disposable, i.e., on the flat side, on which the sample receiving zone is located. It can have a capillary channel which can have a sample inlet and a sample outlet. The body fluid can enter into the capillary channel through the sample inlet after the piercing; it can exit from the channel again through the sample outlet.

The body fluid exiting from the capillary channel through the sample outlet can be transferred to the sample receiving zone, if the sample outlet is close to the sample receiving zone of the test strip. This position, in which the piercing element can be positioned relative to the test strip so that the sample outlet approaches the sample receiving zone, can be referred to as the sample transfer position. The movement path of the piercing element therefore can comprise this position.

The analysis system according to the disclosure and also the disposable integrated sample acquisition and analysis element can be distinguished by a simple construction. If the piercing element penetrates into the body part with its tip during the puncture movement and generates a wound, body fluid may penetrate to the sample inlet into the capillary channel. The body fluid can be thus guided intentionally into the capillary channel already upon piercing. During the retraction phase of the puncture movement of the piercing element, further body fluid can also penetrate into the capillary channel and can be guided thereby to the sample outlet.

According to the disclosure, the exit of the body fluid from the capillary channel can take place in the sample transfer position. If the piercing element is positioned in this position, at least a part of the sample outlet can be located at the sample receiving zone in such a manner that the body fluid may pass from the capillary channel onto the sample receiving zone. This transfer point can thus be a defined position, so that it may be easily ensured that the body fluid reaches the sample receiving zone. It can be proven to be advantageous that the piercing and the receiving of the body fluid can occur using the same element, namely using the piercing element.

The advantage thus can result for the user of the analysis instrument that it can be very simple to operate. He only has to place the instrument once on his body part, preferably on the fingertip, to perform a complete analysis. Further handling steps of the user, such as removing the device after the puncture, mechanical milking, and putting the device back on the puncture wound to receive the exiting body fluid in a capillary channel, can be dispensed with. Real "one-stop handling" can thus be possible for the user. Therefore, high acceptance with the users can be provided. The analysis system according to the disclosure can be intended in particular for older people, whose fine-motor ability can be weakened.

The reliable transfer of the body fluid to the sample receiving zone can be supported in that the movement of the piercing element can occur on the side of the test strip which can be referred to as the sample contact side and can comprise the sample receiving zone. A simple and reliable transfer can thus be possible.

In an one exemplary embodiment, the sample acquisition can be improved in that a collection movement can follow the piercing movement of the piercing element, during which a body fluid sample can be received in the capillary channel of the piercing device. The movement velocity of the piercing element can be less during the collection movement than during the piercing movement. The relative movement of the piercing element relative to the test strip can also be slower during the collection movement in comparison to the puncture movement. In an exemplary embodiment, both can be moved synchronously so that their relative position can be maintained. In this case, no relative movement can occur between piercing element and test strip during the collection movement.

Optionally, the piercing element can also perform a transfer movement in addition to the piercing movement and the collection movement, in which the piercing element can be moved into the sample transfer position, in which the transfer of the body fluid from the capillary channel to the sample receiving zone can take place. The path of all movements of the piercing element, which comprises the piercing movement, the collection movement, and the transfer movement, can be referred to as the movement path of the piercing element.

In another exemplary embodiment of the analysis system, the analysis instrument can comprise a coupling unit having two coupling mechanisms. The first coupling mechanism can be adapted for coupling with the piercing element, and the second coupling mechanism for coupling with the test strip. The test element and the test trip may thus be moved independently of one another, wherein both components may be able to be moved simultaneously at equal or different velocities. The movements may take place relative to a housing of the piercing device, for example. A coupling unit of this type may be used if the piercing element is to execute the explained collection movement. Alternatively to a coupling unit comprising two coupling mechanisms, for example, the test strip may be fixed in the housing of the analysis instrument. This may be possible in simpler embodiments, for example, if the test strip does not have to be moved for the sample receiving.

In one embodiment, the analysis system can comprise a stacking magazine, which may be replaceable and receives multiple disposables (i.e., sample acquisition and analysis elements). The stacking magazine may be received in a retainer of the analysis instrument, for example, so that multiple disposables can be available in the instrument. As soon as all disposables of a stacking magazine have been consumed, the magazine can be replaced, in that it can be removed from the retainer and can be replaced by a new magazine equipped with unused disposables. Optionally, the stacking magazine may also provide a receptacle for the used and consumed sample acquisition and analysis elements.

The disposables can be removed individually from the stacking magazine using a transport apparatus and may be moved into a coupling position. In this coupling position, they may be coupled by the coupling unit for reaching in a further step an operating position, for example, in which they can be ready for use. The supply of the unused disposables may be automated by a suitable transport apparatus and an adapted coupling unit. The transport apparatus may also be suitable for magazining used disposables after their use again, for example, in an area provided for this purpose inside the stacking magazine.

The storing in the magazine can be made easier in that the test strip of the disposable can be implemented as flat. The piercing element can also be relatively flat, so that the entire disposable can have a very low thickness in comparison to its length and width. The disposable may be stacked especially well and easily.

Optionally, the stacking magazine and/or the analysis instrument may be provided with a display, which can display either the number of still unused disposables or the already used disposables. The display may be performed in the form of numbers or other markings or indicators, as are known in the prior art. Various stacking magazines are also known in the prior art, which may be suitable for use in the analysis system according to the disclosure, e.g., from EP 0974061 or U.S. Pat. No. 6,827,899.

Accordingly, it a feature of the embodiments of the present disclosure to have an analysis system with improved user comfort and improved ease of use that is relatively simple and cost-effective. Other features of the embodiments of the present disclosure will be apparent in light of the description of the disclosure embodied herein.

BRIEF DESCRIPTION OF THE SEVERAL VIEWS OF THE DRAWINGS

The following detailed disclosure of the specific embodiments of the present disclosure can be best understood when read in conjunction with the following drawings. The special features illustrated therein may be used individually or in combination to provide preferred embodiments of the disclosure, which like structure is indicted with like reference numerals and in which:

FIGS. 4a-h illustrate a schematic sectional illustration of a part of the piercing system of FIG. 1 in eight usage positions according to an embodiment of the present disclosure;

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

The location specifications "front" and "rear" used-hereafter relate to the puncture direction, in which the piercing element can be moved to generate a wound in a body part. The front end of the piercing element can thus be the end which, upon movement of the piercing element in the puncture direction, can be adjacent to a housing opening, to which a body part may be pressed against to generate a wound.

Figure 1:
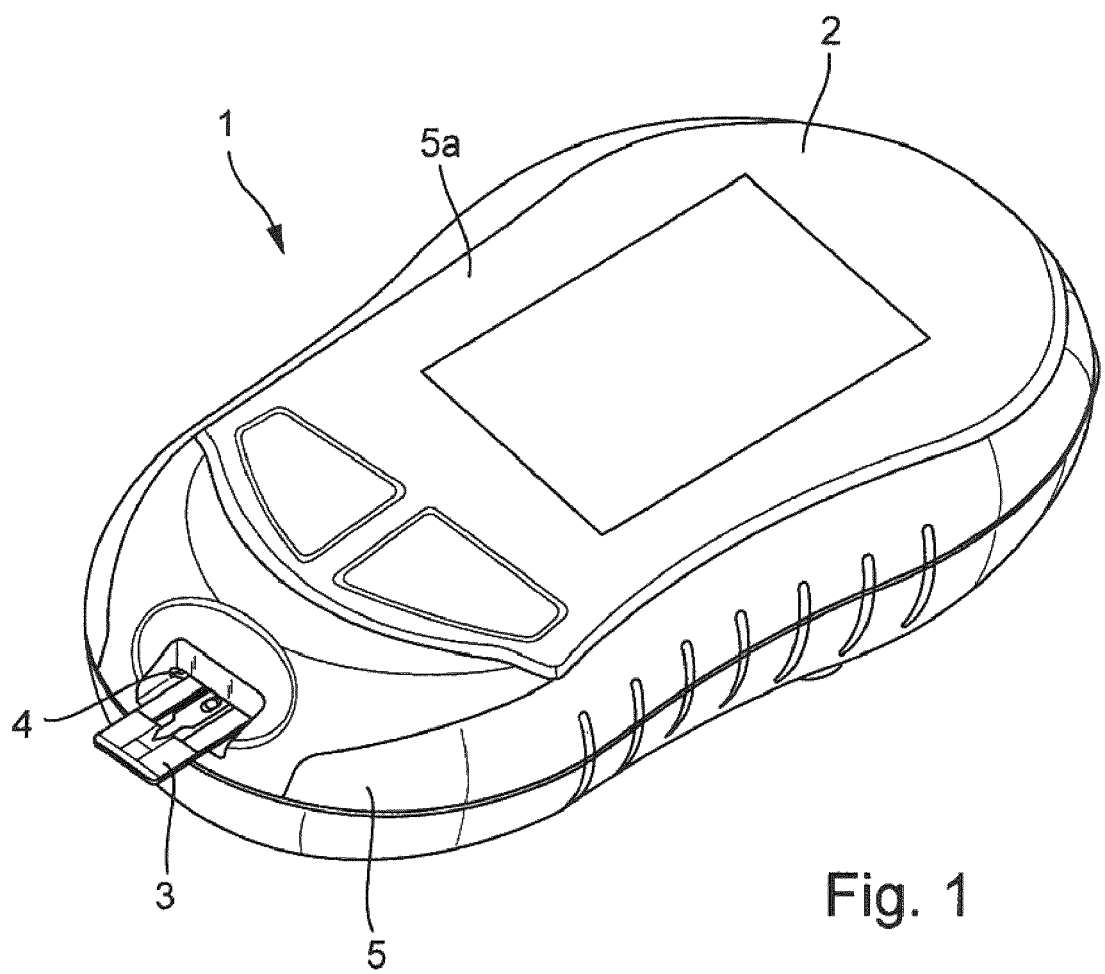
FIG. 1 illustrates an analysis system comprising an analysis instrument and an integrated sample acquisition and analysis element according to an embodiment of the present disclosure.
Figure 2A:
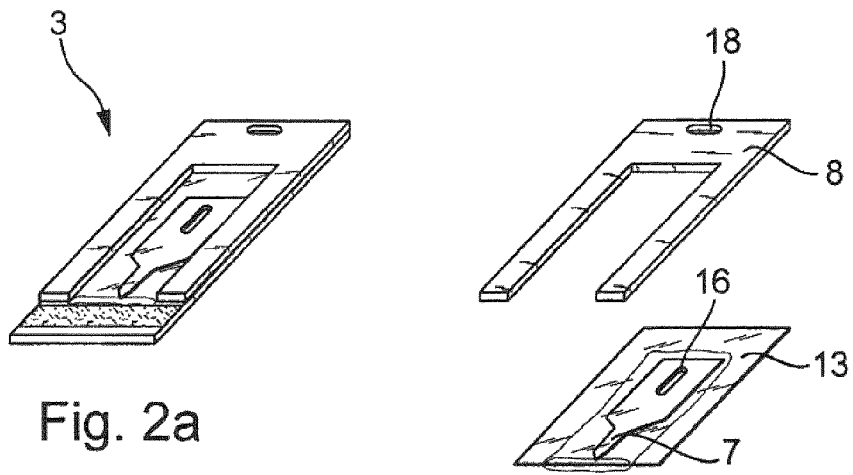
FIGS. 2a-d illustrate an exploded illustration of the sample acquisition and analysis element of FIG. 1 according to an embodiment of the present disclosure.
Figure 2B:
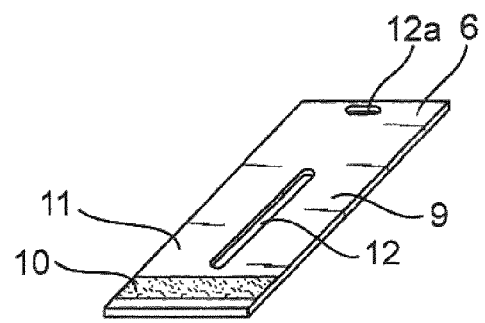
Figure 2C:
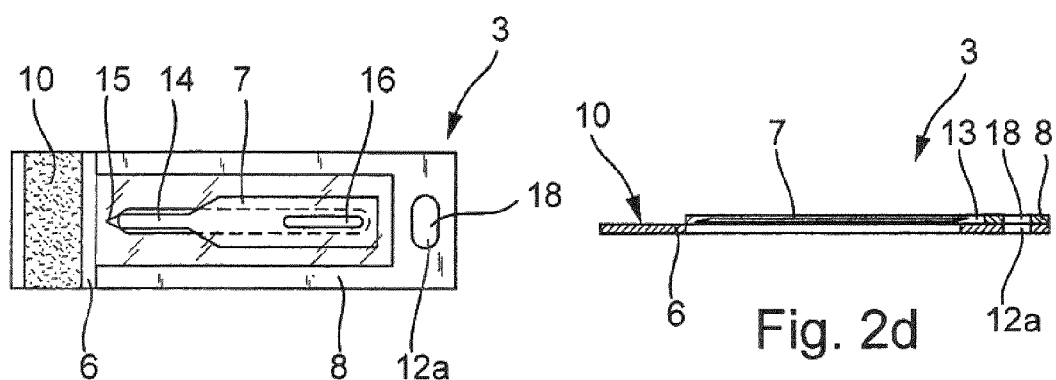
Figure 2D:
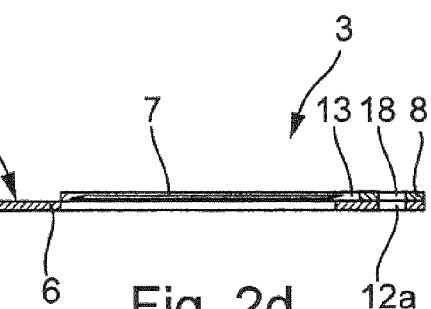

Referring initially to FIG. 1, an analysis system 1 comprising an analysis instrument 2 and a disposable integrated sample acquisition and analysis element 3, which can be referred to as a disposable, is illustrated. The disposable 3 can partially project from an opening 4 of a housing 5 of the analysis instrument 2. Operating elements for operating and controlling the analysis instrument 2 can be located on the top side 5a of the housing 5.

FIGS. 2a-d and FIG. 3 show various embodiments of the disposable 3. In a first embodiment, the disposable 3 can comprise an elongated test strip 6, a piercing element 7, and a cover part 8. The test strip 6, whose length, in one exemplary embodiment, can be three to four times greater than its width, can have a sample receiving zone 10 on one of its two substantially flat sides 9. This substantially flat side 9 can be referred to as the sample contact side 11. The sample receiving zone 10, in one embodiment, can be located in the front area of the test strip 6. The part of the test strip 6 which can be close to the front end of the test strip 6 in the puncture direction can be referred to as the front area. This area may begin directly at the front end of the test strip 6; however, it may also be spaced apart from the front edge. In any case, the sample receiving zone 10 can be located closer to the front end of the test strip 6 than the rear end.

The test strip 6 can have a longitudinal groove 12 approximately in the middle which can extend in the longitudinal direction. The longitudinal groove 12 can be used as a passage of a coupling mechanism, which can move the piercing element 7.

A hole 12a can be located in the area of the far end of the test strip 6, which can be, in one embodiment, implemented as an oblong hole and can extend substantially transversely to the puncture direction in the test strip 6. This hole 12a can be used to couple a coupling mechanism on the test strip 6, in order to move the test strip 6 in the analysis instrument 2 and/or to position or fix it.

The piercing element 7 can be enclosed by a protective envelope 13, such as, for example, a thin sealing film. The protective envelope 13 can, in one embodiment, comprise a film which can be torn easily and can be further torn easily, so that before or at the beginning of the piercing movement, the tip 15 of the piercing element 7 may pierce through the protective envelope 13, in order to exit therefrom. During the production process of the disposable 3, the piercing element 7 may be hermetically enclosed separately by the protective envelope 13 and subsequently sterilized so that it may be stored aseptically.

The substantially flat piercing element 7 can have a needle element 14 having a tip 15 on its front end, which can generate a puncture wound in the body part during the puncture movement when it hits the skin of a body part. The piercing element 7 can have a coupling recess 16, in which a coupling element may engage for coupling on a drive unit. In one embodiment, the coupling recess 16 can be an elongated hole.

The needle element 14 of the piercing element 7 can have a capillary channel 17 on its bottom side. In this exemplary embodiment, the capillary channel 17 can be substantially oriented toward the sample receiving zone 10 of the test strip 6.

In one exemplary embodiment, the disposable 3 can be constructed like a sandwich such that the piercing element 7 can have the protective envelope 13 located between the cover part 8 and the test strip 6. The cover part 8 can be open in the puncture direction so that a coupling element which can be coupled from the top side (top layer) on the piercing element 7 may be moved on the movement path jointly with the piercing element 7 in the puncture direction. In one embodiment, the cover part 8 can lie on top on the protective envelope 13 on the test strip 6, in order to improve the stacking ability of the disposable 3. The piercing element 7 cannot be retained, however, so that it may move in substantially longitudinal direction of the disposable 3. Because the cover part 8 does not touch the piercing element 7, no guiding of the piercing element 7 can occur. The U-shaped cover part 8 can have a hole 18 in its base. It can substantially correspond to the hole 12*a*, so that the disposable 3 may be held and moved by a coupling unit which can extend through the holes 12*a*, 18.

In an exemplary alternative embodiment of the disposable according to FIG. 3, the protective envelope and the cover part can be formed from a contoured main film 19 and a cover film 20. The main film 19 can be formed from a base on which a U-shaped spacer part made of film can rest. The base and the spacer part can be integrally connected to one another. The piercing element 7 can be located between the two U-legs of the spacer part, which can form spacers 21. The piercing element 7 can thus be substantially enclosed at least on its longitudinal sides by spacers 21, whose thickness can be at least as great as the thickness of the piercing element 7. The dimension perpendicular to the sample contact side 11 of the test strip 6 can be defined as the thickness. In this way, upon the joining of the main film 19 and the cover film 20, a protective envelope 13 having a cavity can be formed, in which the piercing element 7 can be movable. In one embodiment, the main film 19 and the cover film 20 can be implemented integrally, the front part of the main film 19 can be used as the cover film 20 can be wrapped around so that it can rest on the main film 20 and the wraparound edge can be located on the front side in the puncture direction. The two films may then be glued to one another on the three remaining open sides. The piercing element 7 can pass through the turned-over edge on its puncture path, so that the piercing element does not have to exit through any of the glued sides.

In this embodiment, the piercing element 7 can be spaced apart from the sample contact side 11 of the test strip 6 by the thickness of the base of the main film 19. The piercing element 7, which, in one embodiment, can be implemented as substantially flat, can have a bottom side 22 shown in FIG. 3*a*, which can face toward the sample contact side 11. In one embodiment, the bottom side 22 can be spaced apart from the sample receiving zone 10 in such a manner that the piercing element 7 does not touch the sample receiving zone 10 at least during the propulsion phase of the piercing movement. The spacing between the bottom side 22 and the sample receiving zone 10, which can be defined as being substantially perpendicular to the flat side 9 of the piercing element 7, can be such that even if the piercing element 7 can be located directly above the sample receiving zone during the piercing movement, an intermediate space can exist. Thus, on the one hand, the piercing element 7 can be prevented from rubbing along the sample receiving zone 10 and damaging it, on the other hand, the piercing movement of the piercing element 7 can be prevented from being influenced by friction, in particular in that the piercing element 7 can be braked.

Figure 3A:
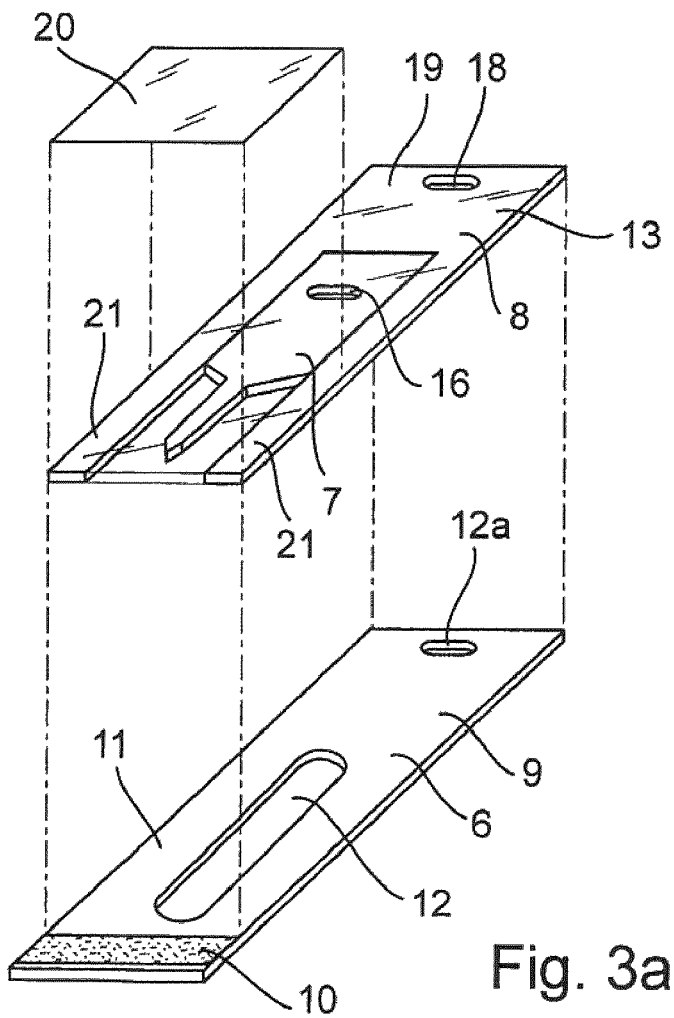
FIGS. 3a and b illustrate an alternative embodiment of a sample acquisition and analysis element according to an embodiment of the present disclosure.
Figure 3B:
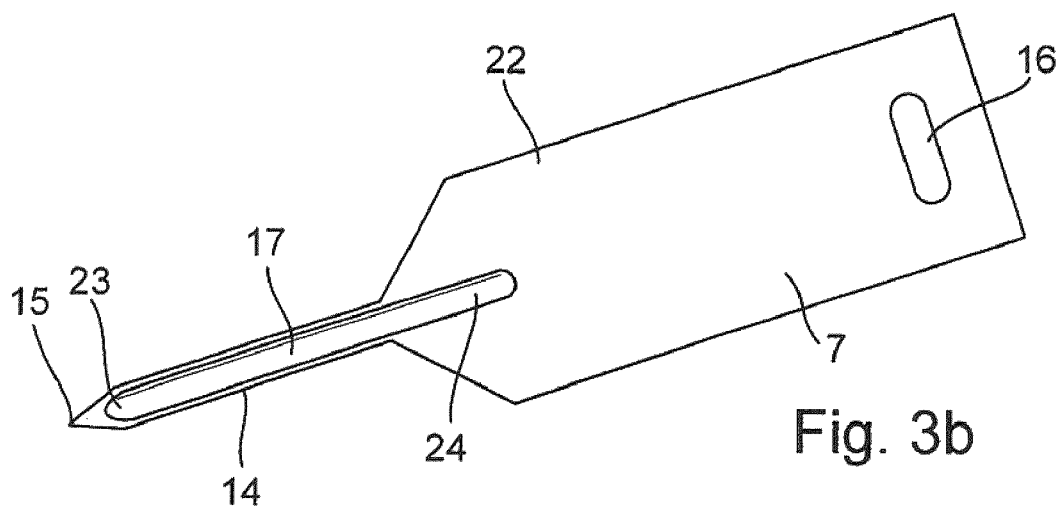

FIG. 3*b* shows the piercing element 7 viewed from its bottom side 22. The capillary channel 17 can extend from the tip 15 of the piercing element along the needle element 14 up to its main body. The capillary channel 17 can have a sample inlet 23, through which the body fluid may penetrate after the puncture into the capillary channel 17. The sample inlet 23 can be located on the tip 15. On the end of the capillary channel 17 which can be opposite to the sample inlet 23, the capillary channel 17 can have a sample outlet 24, through which the body fluid may exit from the capillary channel 17. In the embodiment shown, the capillary channel 17 can be open on one side, so that a grooved capillary channel 17 can be formed. The open top side of the capillary channel 17, implemented here as a substantially semi-cylinder, thus can represent the sample inlet 23 and the sample outlet 24, which can merge into one another. The sample inlet 23 and the sample outlet 24 can thus not only be limited to the two ends of the capillary channel 17.

The disposable shown in FIGS. 2 and 3 can be distinguished from the prior art in that it can be especially flat. It may be stacked well and may therefore can be magazined easily.

FIGS. 4*a-h* schematically show the front end of the analysis instrument 2 during different movement phases of the disposable 3.

Figure 4A:
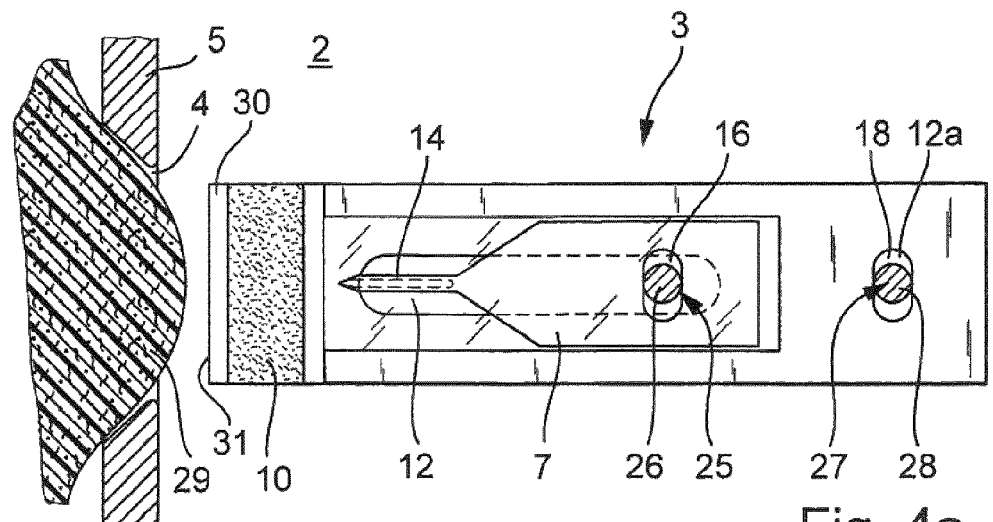

FIG. 4*a* shows the disposable 3 in a coupling position, after the disposable 3 has been removed from a stacking magazine (not shown here). In the coupling position, the disposable 3 can be coupled by a coupling unit. The coupling unit can have a first coupling mechanism 25 for coupling with the piercing element 7, which can be implemented in the form of a mandrel 26. The mandrel 26 can engage through the coupling recess 16 of the piercing element 7. The mandrel 26 can also extend in the substantially longitudinal groove 12 of the test strip 6, in which it may move during the puncture movement of the piercing element 7. Upon insertion of the mandrel 26 into the coupling recess 16 and the longitudinal groove 12, the protective envelope 13 implemented as a film can be pierced. Up to this moment, the piercing element 7 can be sterile in its protective envelope 13.

In one embodiment, a second coupling mechanism 27 can also be implemented as a mandrel 28. The mandrel 28 can be guided in such a manner, preferably simultaneously with the mandrel 26, in that it can pierce into the hole 18 of the protective envelope 13 and the corresponding hole 12*a* of the test strip. In this way, the test strip 6 may be retained and guided so that the test strip 6 may also perform a movement in and opposite to the puncture direction. The coupling mechanisms 25 and 27 of the coupling unit can allow the coupling of the disposable 3 on a drive unit (not shown here), in which the movement of the piercing element 7 and of the test strip 6 can be driven.

Because the protective envelope 13 can be very thin and can have little tear resistance, it can offer no resistance to the mandrels 26, 28. The coupling of the disposable 3 to the coupling unit cannot be obstructed.

In the coupling position according to FIG. 4*a*, the disposable 3 can still be far enough from the opening 4 of the housing 5 so that a body part pressing against the opening 4, such as a fingertip 29, which can bulge into the opening 4, does not come into contact with the disposable 3. Of course, the housing 5 of the analysis system and the opening 4 may be implemented in such a manner that the fingertip 29 does not bulge into the inner chamber of the analysis instrument 2.

At the beginning of the puncture procedure, the mandrel 28 of the second coupling mechanism 27 can be moved in the direction toward the opening 4, whereby the test strip 6 can be moved far enough in the puncture direction that the front end 30 of the test strip 6 can press against the fingertip 29. This front end 30 in the puncture direction can be implemented in one embodiment as a skin contact surface 31. In one exemplary embodiment, the front edge 32 of the test strip 6 can be the skin contact surface 31. In one embodiment, the skin contact surface 31 can press against the body part at least during a part of the movement path of the piercing element and can be used as a piercing depth reference element 33 for the propulsion phase of the piercing movement. A predetermined value of the piercing depth can be determined by the distance in the puncture direction between the skin contact surface 31 and the position of the tip 15 of the piercing element 7 at the reversal point of the piercing movement. A desired piercing depth of the piercing element 7 into the fingertip 29 may thus be set and changed.

After or simultaneously with the movement of the mandrel 28, the mandrel 26 of the first coupling mechanism 25 can also be moved in the puncture direction so that the piercing element 7 can be moved along a part of its movement path in the puncture direction. The protective film 13 can be torn open further by the mandrel 26. On its front end, it can be penetrated by the tip 15 of the piercing element 7. In one exemplary embodiment, the piercing element 7 can be moved in the puncture direction until the tip 15 of the piercing element 7 can be positioned at the front edge of the sample receiving zone 10. In one embodiment, the tip 15 can be located approximately 0.5 mm away from the front edge 32 of the test strip 6 so that the test strip 6 can project beyond the piercing element.

Figure 4B:
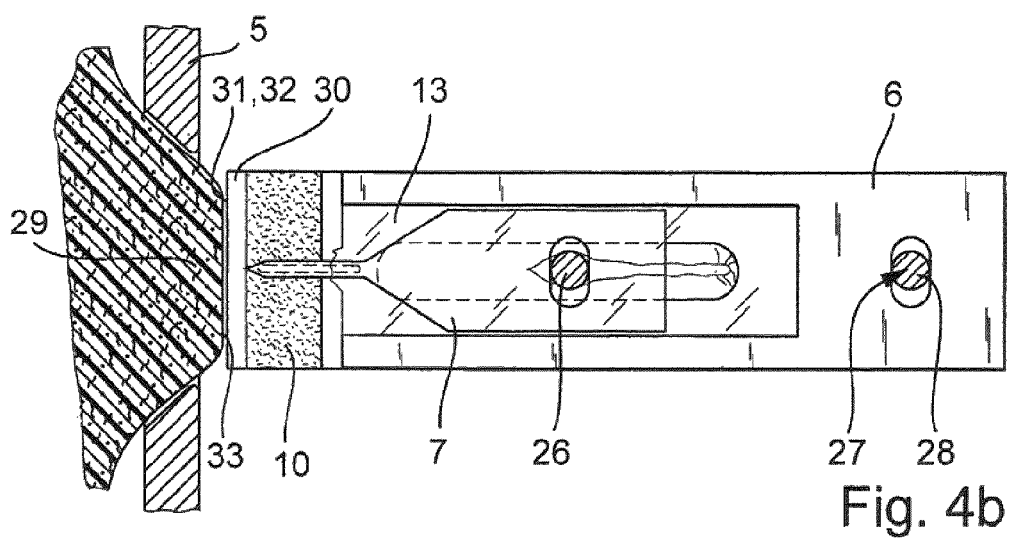

FIGS. 4a and 4b show that the user can press his fingertip 29 on the analysis instrument 2 before the disposable 3 can be moved into its starting position (FIG. 4b). Alternatively, the movement of the disposable 3 from the coupling position into the start position may also occur first. After this, the user can press his fingertip 29 against the opening 4 of the analysis instrument 2, until the fingertip 29 can contact the skin contact surface 31. Before a piercing may occur, for example, it may need to be electronically checked that the fingertip actually touches the skin contact surface 31. Optionally, the disposable 3 may also be mounted spring-loaded in the analysis instrument in this embodiment.

Figure 4C:
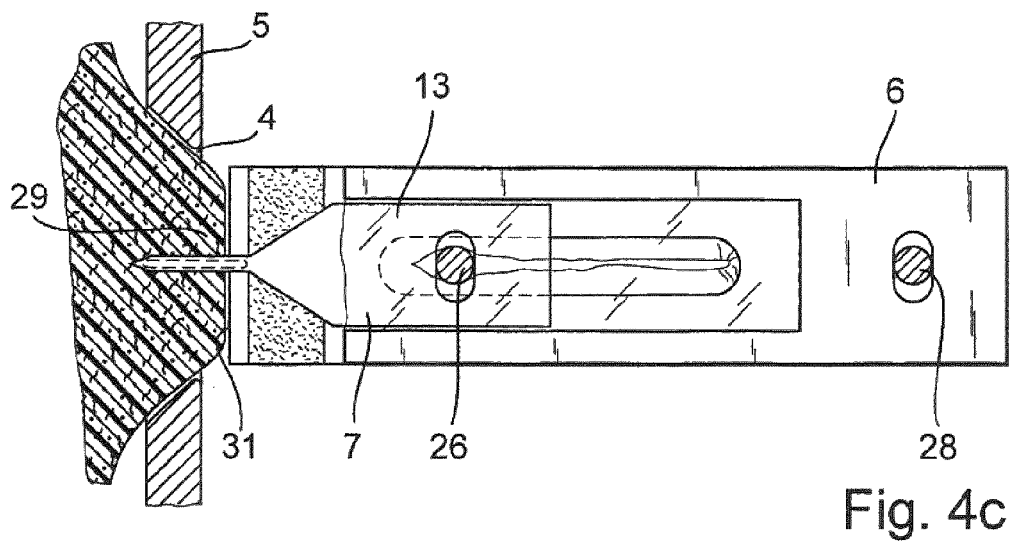

During the propulsion phase of the puncture shown in FIG. 4c, the first coupling mechanism 25 can be moved in the substantially longitudinal groove 12 in the puncture direction until the tip 15 of the piercing element can penetrate into the fingertip and can generate a puncture wound. In this exemplary embodiment, the tip 15 of the piercing element 7 can thus be moved during the propulsion phase of the piercing movement beyond the front end 30 of the test strip 6 in the puncture direction.

As soon as the set piercing depth is reached, the retraction phase of the piercing element 7 can begin, during which the mandrel 26 of the coupling mechanism 25 can be moved opposite to the puncture direction. Only the mandrel 26 and the piercing element 7 can be moved during the entire puncture, which can take place at a very high velocity. Thus, a rapid relative movement of the piercing element 7 to the test strip 6 can take place, the mandrel 26 can be moved relative to the mandrel 28. In one exemplary embodiment, the test strip 6 itself cannot be moved or can only be moved very slowly during the piercing, so that the skin contact surface 31 of the test strip 6 can contact the fingertip 29 and thus can exert a pressure on the fingertip.

In one embodiment, a collection movement can follow the piercing movement of the piercing element 7. During the collection movement the relative movement between the piercing element 7 and the test strip 6 can be significantly slower than in the piercing movement. Alternatively, no relative movement can occur at all. The piercing element 7 and the test strip 6 can be moved synchronously with one another. Alternatively, the test strip 6 of the disposable 3 may remain in its position.

If the test strip 6 can also be moved opposite to the puncture direction during the collection movement, the pressure exerted by the skin contact surface 31 on the fingertip can be reduced. The blood can thus be encouraged to exit from the wound. The blood may penetrate into the capillary channel 17 of the piercing element 7. An effective "collection" of blood may thus be implemented. Manual and/or mechanical "milking" may not be necessary. The skin contact surface 31 can thus be used as an expression aid in this case.

During the collection movement of the piercing element shown in FIG. 4d, the blood can exit out of the puncture wound through the sample inlet 23 into the capillary channel 17. The blood can be moved along the channel in the direction toward the sample outlet 24 by the capillary action.

At the end of the collection movement, which is shown in FIG. 4e, the disposable 3 can be moved far enough from the opening 4 that there can no longer be contact with the fingertip 29. The fingertip 29 may be taken away from the opening 4. The collection movement can be completed. The capillary channel 17 can filled with blood.

In the example shown, the tip 15 of the piercing element 7 can have a protrusion in relation to the test strip 6, which, in one embodiment, can be maintained at least in the last part of the collection movement.

Following the collection movement, the piercing element 7 can be moved in a transfer movement into the sample transfer position, as shown in FIG. 4f. The mandrel 26 can be moved in relation to the mandrel 28 therein until the tip 15 of the piercing element 7 approximately can correspond to the front edge of the sample receiving zone 10.

In addition, the disposable 3 can be moved away from the housing opening until it can reach a position in which the sample receiving zone 10 can be positioned in the area of a contact pressure apparatus 34 of the analysis instrument 2. This movement can be caused by a movement of the mandrel 26. The movement of the disposable 3 may take place before, after, or simultaneously with the movement of the piercing element 7 described above.

Figure 4G:
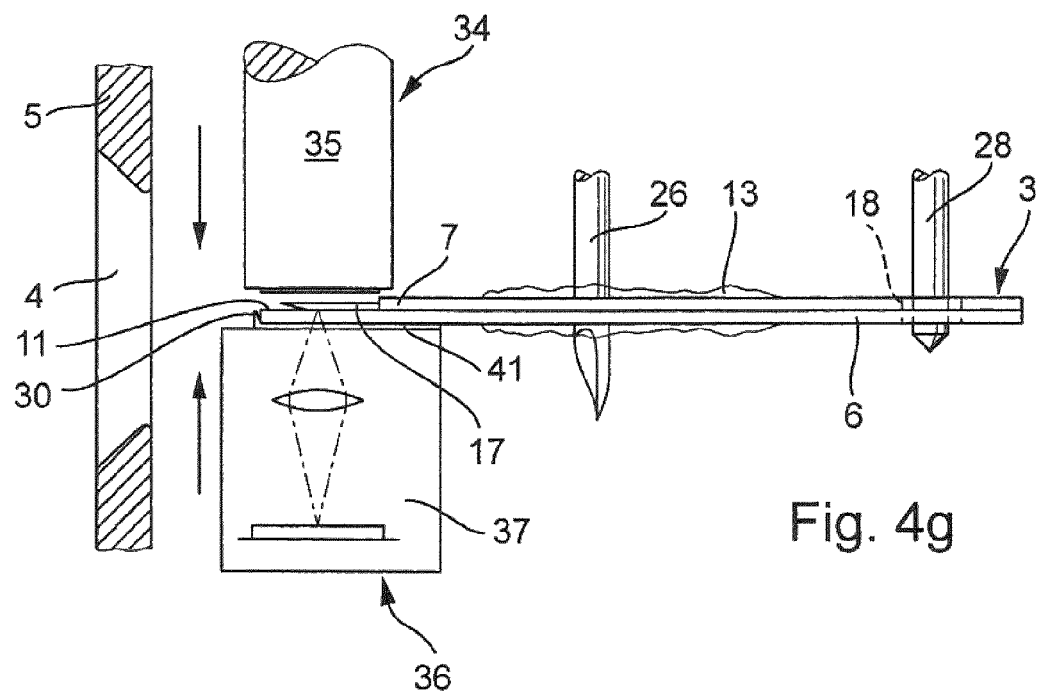

In the sample transfer position of the piercing element shown in FIGS. 4f and 4g, the sample outlet 24 of the capillary channel 17 can be substantially adjacent to the sample receiving zone 10 in such a manner that blood from the capillary channel 17 may be transferred through the sample outlet 24 to the sample receiving zone 10. The capillary channel 17 can be located on the bottom side of the piercing element 7, i.e., on the side facing toward the sample contact side 11 of the test strip 6. The sample outlet 24 can be positioned directly above the sample receiving zone 10. A simple transfer of the blood can be possible. In one embodiment, the capillary channel 17 can be open on one side in such a manner that its opening can be substantially oriented toward the sample receiving zone 10.

In one embodiment, the piercing element 7 can be spaced apart from the test strip 6 in the direction that can be substantially perpendicular to the sample contact side 11 in such a manner that the piercing element 7 does not touch the sample receiving zone 10. The piercing element 7 can now be pressed, in the sample transfer position, from above (in the direction of the arrow) against the sample receiving zone 10 by a plunger 35 of the contact pressure apparatus 34. The sample outlet 24, which can be formed by one part of the one-sided opening of the capillary channel 17, can be moved to the sample receiving zone 10 so that the blood can be reliably transferred.

A measuring and analysis unit 36, which, in one exemplary embodiment, can comprises an optical measuring unit 37, can be located opposite to the contact pressure apparatus 34 (i.e., under the disposable 3). In one exemplary embodiment, the optical measuring apparatus 37 can be located on the bottom side of the test strip 6. It can be used for performing a photometric measurement, in order to measure an optically measurable measurement variable, which can be characteristic for the determination of the analyte in the body fluid and in the blood, respectively.

Figure 7:
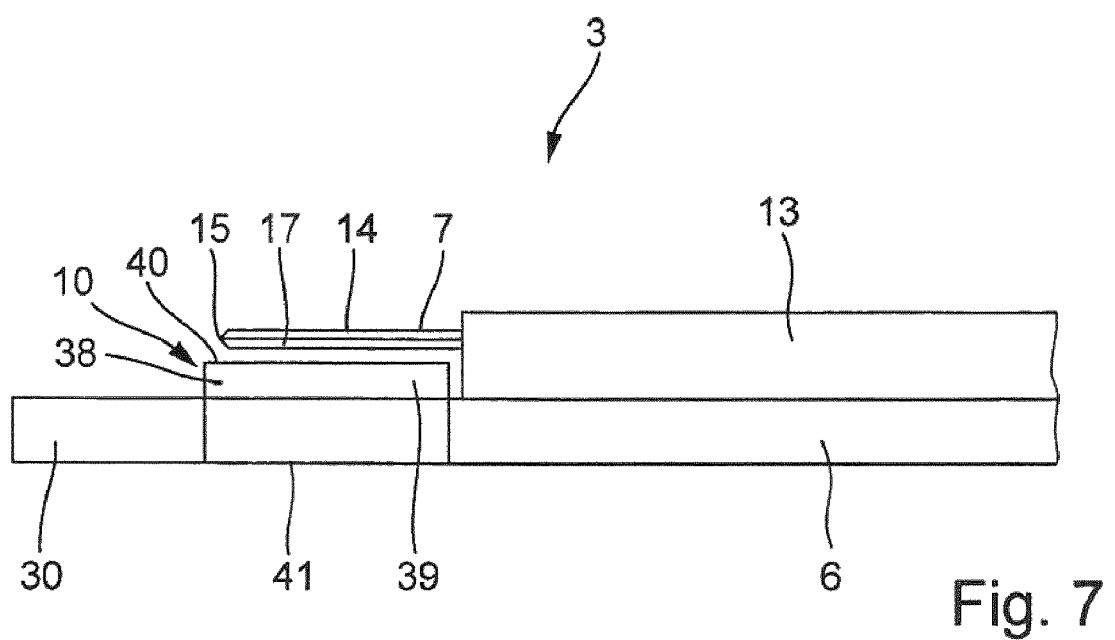
FIG. 7 illustrates a detailed view of the front end of a sample acquisition and analysis element according to an embodiment of the present disclosure.

FIG. 7 shows in detail the front end 30 of the disposable 3 having the sample receiving zone 10, against which the measuring apparatus 37 can press. In one exemplary embodiment, the sample receiving zone 10 can comprise a test field 38, which can comprise at least one absorbent layer 39. The test field 38 can have a sample receiving surface 40 on the sample contact side 11 of the test strip 6 and a detection surface 41 on the bottom side, which can be opposite to the sample contact side 11. In one exemplary embodiment of the disposable 3, the sample receiving zone 10 and the test field 38 can be identical. However, it can also be possible that the test field 38 and the sample receiving zone 10 can deviate from one another, so that the detection surface 41 for the optical measurement of the characteristic measurement variable can be spatially separated from the sample receiving surface 40.

In one exemplary embodiment, the photometric measurement using the optical measuring apparatus 37 can occur by diffuse reflection on the detection surface 41. The detection surface 41 can be especially preferably in fluid connection with the test field 38 and/or the sample receiving zone 10. Diffuse reflection can be understood as a measurement using a measuring configuration, in which the angle of incidence of an (electromagnetic) wave (e.g., light) can be different from the exit angle after incidence on the detection surface 41.

Because the optical measurement can occur on the bottom side, i.e., on the side opposite to the sample contact side 11 of the test strip 6, pigments which can be contained in the blood, for example, do not corrupt the measurement result. These pigments can remain in the absorbent layer 39 and/or on the sample receiving surface 40. Suitable embodiments of test fields 38 of this type are generally known in the prior art.

Figure 4H:
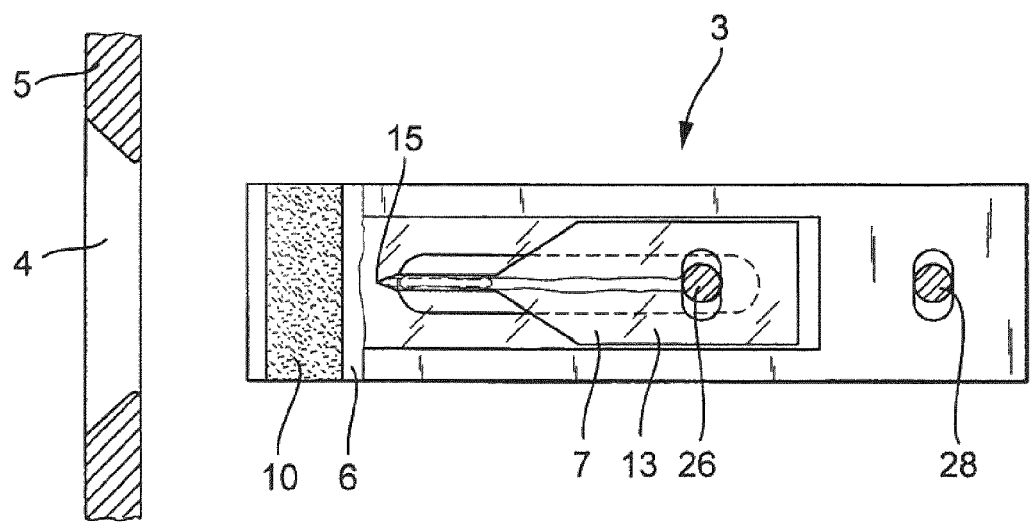

After the photometric measurement has been performed in the sample transfer position of the piercing element 7, the piercing element 7 can be moved relative to the test strip 6 in the direction of the rear end of the disposable 3 until the piercing element 7 can be located in its starting position again, in which it can be completely retracted into the (partially damaged) protective envelope 13, FIG. 4h.

The disposable 3 can then moved back into the coupling position, from which it may then be moved by a transport apparatus back into the stacking magazine and into a receptacle container for consumed disposables, respectively.

Figure 5:
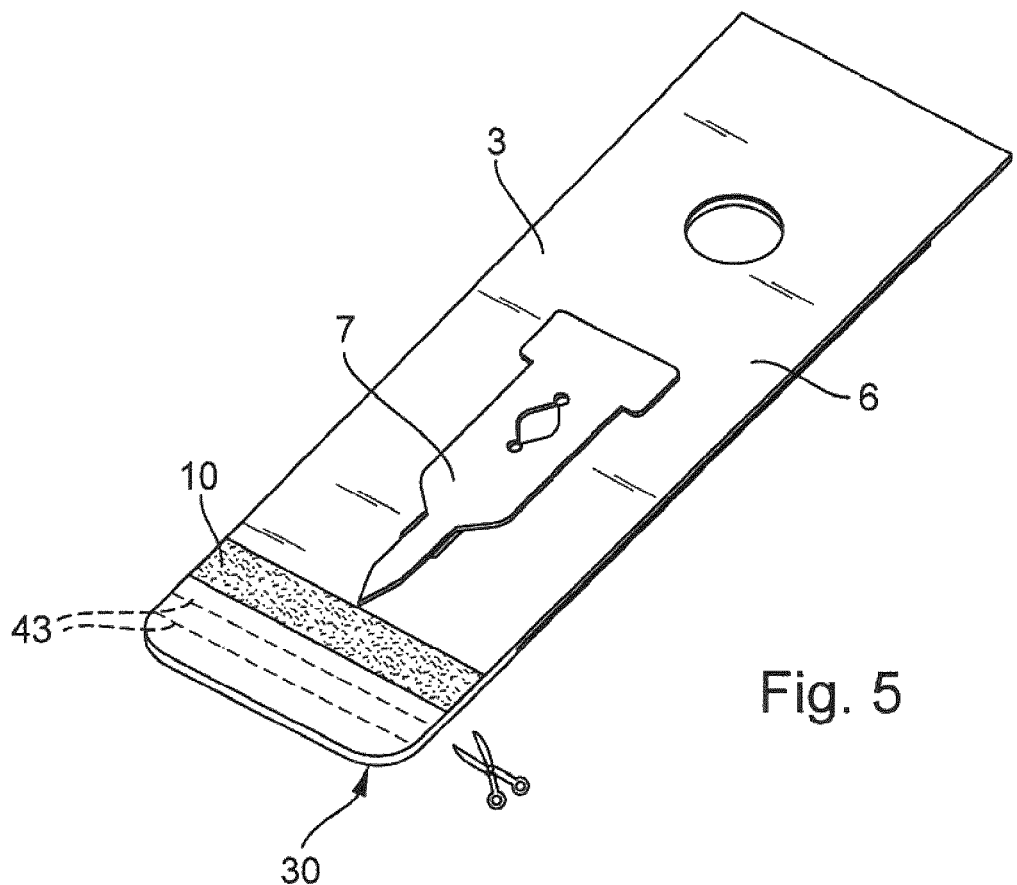
FIG. 5 illustrates an alternative embodiment of a sample acquisition and analysis element according to an embodiment of the present disclosure.

FIG. 5 shows a schematic illustration of a further embodiment of the disposable 3. In one exemplary embodiment, the test strip 6 of the disposable can be implemented so that the length of the disposable, i.e., the dimension in the puncture direction, may be varied by breaking or cutting off the front end 30 of the test strip 6. Different piercing depths may thus be set, without having to provide a further piercing depth setting device in the analysis instrument 2. Multiple markings and/or perforations of the test strip 6 can be located in the area of the front end 30, at which the disposable 3 may be shortened in such a manner that the piercing depth may be set individually during the puncture procedure. Each marking or perforation can correspond to a predetermined piercing depth. The individual piercing depth setting can thus be performed by a length change on the disposable 3.

In one exemplary embodiment, a sample receiving zone 10 can also be provided in this type of disposable, the markings or perforations for shortening the disposable not extending up into the sample receiving zone 10. Even upon setting of the greatest piercing depth (shortest test strip 6), the sample receiving zone 10 can be spaced apart from the front edge 33 of the disposable.

Figure 6:
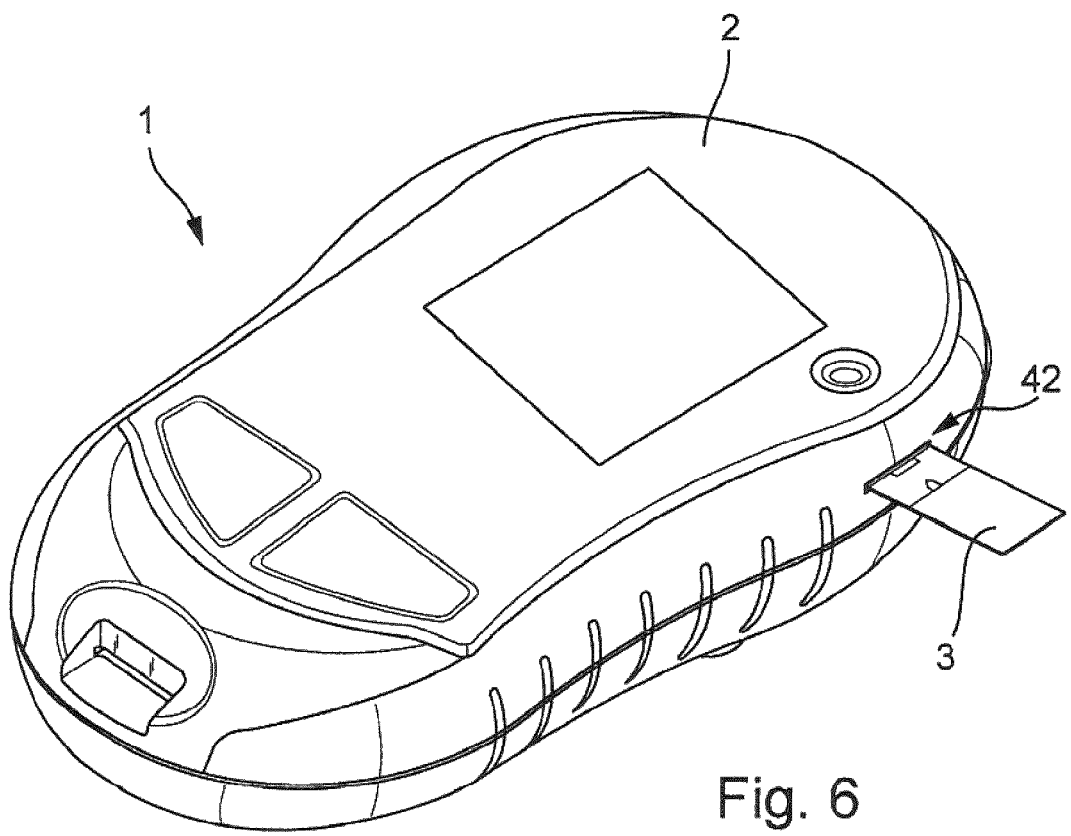
FIG. 6 illustrates a further embodiment of an analysis instrument according to an embodiment of the present disclosure.

In order to achieve the most precise possible setting of the piercing depth, in an embodiment of the analysis system 1 according to FIG. 6, a shortening unit 42 can be provided, which can be integrated substantially laterally in the analysis system 1, for example. The preferred shortening unit 42 can be used to shorten the test strip 6 on its front end 30 in the puncture direction, in order to set the desired piercing depth during the puncture.

Alternatively, the shortening unit 42 may be integrated in the analysis system in such a manner that a disposable 3 transported out of a stacking magazine may be shortened automatically to a settable length. The desired length, which can correspond to a piercing depth, may be set by the user of the analysis instrument on a setting device, for example.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. An analysis system for determining an analyte in a body fluid, comprising:
    a disposable integrated sample acquisition and analysis element comprising,
        a flat test strip having a front end and a sample receiving zone to receive a body fluid sample for analysis, wherein the sample receiving zone is located on a flat side of the test strip to form a sample contact side, wherein the sample receiving zone is adjacent to the front end of the test strip in a puncture direction, and
        a piercing element located parallel to the test strip and adjacent to the sample contact side of the test strip, the piercing element comprising, a tip for generating a bodily puncture wound, and
a capillary channel comprising,
   a sample inlet for body fluid entry after the piercing into the capillary channel, and
   a sample outlet for body fluid exit from the capillary channel,
wherein the piercing element is movable relative to the test strip on a movement path during at least a part of a puncture movement and is positioned in the puncture direction behind the sample receiving zone in such a manner that the sample receiving zone is located between the piercing element and the front end of the test strip,
a reusable analysis instrument comprising,
   a coupling unit adapted to couple the integrated sample acquisition and analysis element to a drive for driving the piercing element in a piercing movement, wherein the piercing movement comprising,
      a propulsion phase in which the piercing element is moved on a puncture path in the puncture direction,
      a retraction phase in which the piercing element is moved opposite to the puncture direction after reaching a reversal point of the piercing movement, and
      a sample transfer position, wherein the sample outlet is adjacent to the sample receiving zone of the test strip such that body fluid may be transferred from the capillary channel through the sample outlet to the sample receiving zone, and
   a measuring and analysis unit for measuring a measurement variable characteristic for the determination of the analyte and for determining a desired analysis result on the basis of the measurement.

2. The analysis system according to claim 1, wherein the measuring and analysis unit comprises,
   an optical measuring apparatus for measuring a photometric measurement with an optically measurable measurement variable which is characteristic for the determination of the analyte.

3. The analysis system according to claim 1, wherein the sample receiving zone has a test field comprising,
   at least one absorbing layer,
   a sample receiving surface on the sample contact side of the test strip, and
   a detection surface on the side of the test strip opposite to the sample contact side.

4. The analysis system according to claim 1, wherein the tip of the piercing element is moved during the propulsion phase of the piercing movement beyond the front end of the test strip in the puncture direction.

5. The analysis system according to claim 1, further comprising
   a collection movement following the piercing movement of the piercing element, wherein the collection movement is slower than the piercing movement or no collection movement of the piercing element relative to the test strip takes place.

6. The analysis system according to claim 5, wherein during the collection movement the body fluid sample is received in the capillary channel of the piercing element.

7. The analysis system according to claim 1, wherein the measuring and analysis unit comprises a contact pressure device in which the piercing element is pressed against the sample receiving zone in a sample transfer position in order to transfer the body fluid to the sample receiving zone.

8. The analysis system according to claim 1, wherein the front end of the test strip in the puncture direction comprises a skin contact surface and is used as a piercing depth reference element, wherein a predetermined value of the piercing depth is determined by a spacing in the puncture direction between the skin contact surface and the position of the tip of the piercing element at the reversal point of the piercing movement.

9. The analysis system according to claim 8, further comprising,
   a shortening unit to reduce the length of the test strip at its front end in the puncture direction.

10. The analysis system according to claim 1, wherein the coupling unit comprises,
    a first coupling mechanism for coupling the coupling unit to the piercing element, and
    a second coupling mechanism for coupling the coupling unit to the test strip.

11. The analysis system according to claim 1, further comprising,
    a plurality of sample acquisition and analysis elements stored in a stacking magazine for individual removal from the stacking magazine, and
    a transport apparatus to moved the plurality of sample acquisition and analysis elements into a coupling position.

12. A disposable integrated sample acquisition and analysis element of an analysis system comprising:
    a flat test strip having a front end and a sample receiving zone to receive a body fluid sample for analysis, wherein the sample receiving zone is located on a flat side of the test strip to form a sample contact side, wherein the sample receiving zone is adjacent to the front end of the test strip in a puncture direction, and
    a piercing element located parallel to the test strip and adjacent to the sample contact side of the test strip, the piercing element comprising,
       a tip for generating a bodily puncture wound, and
       a capillary channel comprising,
          a sample inlet for body fluid entry after the piercing into the capillary channel, and
          a sample outlet for body fluid exit from the capillary channel,
       wherein the piercing element is movable relative to the test strip on a movement path during at least a part of a puncture movement and is positioned in the puncture direction behind the sample receiving zone in such a manner that the sample receiving zone is located between the piercing element and the front end of the test strip.

13. The disposable integrated sample acquisition and analysis element according to claim 12, wherein the capillary channel of the piercing element has a longitudinal opening that opens in a radial direction that extends over at least a part of its length, wherein the opening is oriented toward the sample contact side of the test strip.

14. The integrated sample acquisition and analysis element according to claim 12, wherein the piercing element is enclosed by a protective envelope, wherein the protective envelope is adapted to be penetrated during the puncture movement.

15. The disposable integrated sample acquisition and analysis element according to claim 12, wherein the piercing element is enclosed at least on its longitudinal sides by spacers, wherein the spacers have a thickness that is at least as great as the thickness of the piercing element.

16. The disposable integrated sample acquisition and analysis element according to claim 12, wherein the piercing element is flat, wherein a bottom side of the piercing element faces toward the sample contact side, and wherein the sample receiving zone and the piercing element are spaced apart in such a manner that the piercing element does not touch the sample receiving zone during the propulsion phase of the piercing movement.

17. The disposable integrated sample acquisition and analysis element according to claim 12, wherein the length of the test strip is reduce by breaking or cutting off the front end of the test strip to set different piercing depths.

* * * * *